United States Patent [19]

Wilson et al.

[11] Patent Number: 5,755,228
[45] Date of Patent: May 26, 1998

[54] EQUIPMENT AND METHOD FOR CALIBRATION AND QUALITY ASSURANCE OF AN ULTRASONIC BONE ANAYLSIS APPARATUS

[75] Inventors: Kevin E. Wilson, Cambridge; Donald Barry, Norwood; Dennis G. Lamser, Arlington; John P. O'Brien, Brookline; Jay A. Stein, Framingham, all of Mass.

[73] Assignee: Hologic, Inc., Waltham, Mass.

[21] Appl. No.: 534,131

[22] Filed: Sep. 26, 1995

Related U.S. Application Data

[63] Continuation-in-part of Ser. No. 477,580, Jun. 7, 1995, abandoned.

[51] Int. Cl.$^6$ .................................................. A61B 8/00
[52] U.S. Cl. .................................................. 128/660.06
[58] Field of Search ........................ 128/660.01, 660.02, 128/660.06, 661.03; 73/599, 602

[56] References Cited

U.S. PATENT DOCUMENTS

| | | |
|---|---|---|
| Re. 32,782 | 11/1988 | Pratt, Jr. . |
| 4,361,154 | 11/1982 | Pratt, Jr. . |
| 4,421,119 | 12/1983 | Pratt, Jr. . |
| 4,774,959 | 10/1988 | Palmer et al. . |
| 4,913,157 | 4/1990 | Pratt, Jr. et al. . |
| 4,941,474 | 7/1990 | Pratt, Jr. . |
| 5,014,970 | 5/1991 | Osipov . |
| 5,025,789 | 6/1991 | Hassler . |
| 5,134,999 | 8/1992 | Osipov . |
| 5,349,959 | 9/1994 | Wiener et al. .................. 128/660.06 |
| 5,452,722 | 9/1995 | Langton ............................ 128/661.03 |

FOREIGN PATENT DOCUMENTS

| | | |
|---|---|---|
| 8002796 | 12/1980 | European Pat. Off. . |
| 0299906 | 1/1989 | European Pat. Off. . |
| 0312847 | 4/1989 | European Pat. Off. . |
| 0341969 | 11/1989 | European Pat. Off. . |
| 0516353 | 12/1992 | European Pat. Off. . |
| 0576217 | 12/1993 | European Pat. Off. . |
| 0663182 | 7/1995 | European Pat. Off. . |
| 2257253 | 1/1993 | United Kingdom . |

OTHER PUBLICATIONS

IGEA, DBM Sonic 1200 Brochure (undated).
"Bone" Official Journal of the International Bone and Mineral Society, vol. 16, No. 1, pp. 246–249 Jan. 1995.

(List continued on next page.)

*Primary Examiner*—George Manuel
*Attorney, Agent, or Firm*—Cooper & Dunham LLP

[57] ABSTRACT

An improvement to calibration and quality assurance of an ultrasonic bone analysis apparatus is achieved by using phantoms. A received ultrasound signal that passed through a first phantom is used as a baseline for calculating BUA. The first phantom has an attenuation-versus-frequency profile that is substantially flat in a frequency range of 200 to 1000 kHz and a sound impedance that approximates that of soft human tissue. A propagation time of the signal is used to calibrate a zero point of the apparatus. A second phantom has an attenuation in a frequency range of 200–1000 kHz which approximates that of a human foot, including an attenuation-versus-frequency profile that is substantially linear in the frequency range of 200–600 kHz and is approximately 1 dB/MHz per mm. A received ultrasound signal that passed through the second phantom is used to calibrate the apparatus for a BUA calculation, and can also be used for at least one of determining and correcting a drift of the apparatus. A third phantom has a predetermined SOS that is substantially independent of temperature. A received ultrasound signal that passed through the third phantom is used to calibrate the apparatus for a SOS calculation, and can also be used for at least one of determining and correcting instrument drift. An ultrasonic signal is transmitted through mutually touching transducer pads. The received signal is used as a baseline for calculating BUA. A measurement of the propagation time of the received signal is compared with a temporally-proximate measurement of an ultrasonic signal that passed through a patient's heel to determine a time of propagation through the heel.

61 Claims, 10 Drawing Sheets

OTHER PUBLICATIONS

Ultrasound Assessment of Bone Fragility in the Climacteric Women by DBM Sonic 1200, Mura Marta.

Perth International Bone Meeting, Bone Fragility in the Year 2000, p. 65 (Feb. 1995).

Connective Tissue Changes in the Menopause, M. Brincat et al.

Minhorst Osteoson brochure (May 1995).

Minhorst Osteoson K IV brochure (undated).

Ultrasound for Bone Measurement, A Private Symposium, Lunar, Apr. 1992.

Lunar, Achilles Ultrasound Bone Densitometer brochure (undated).

Clinical Investigations, "Preliminary Evaluation of a New Ultrasound Bone Densitometer" by Belinda Lees and John C. Stevenson, Calif Tissue Int. 1993.

Report on "Ultrasonic Assessment of Bone III", May 1993.

Observations at ASBMR, by G.H. Brandenburger, 1991.

"Ultrasound Measurements of the Os Calcis", by R. Mazess et al., Presented at the Third Bath Conference on Osteoporosis and Bone Mineral Measurements (Jun. 1992).

Perth International Bone Meeting, Bone Fragility in the Year 2000: Clinical Measurement, p. 63 (Feb. 1995).

Perth International Bone Meeting, Bone Fragility in the Year 2000: Clinical Measurement, p. 61 (Feb. 1995).

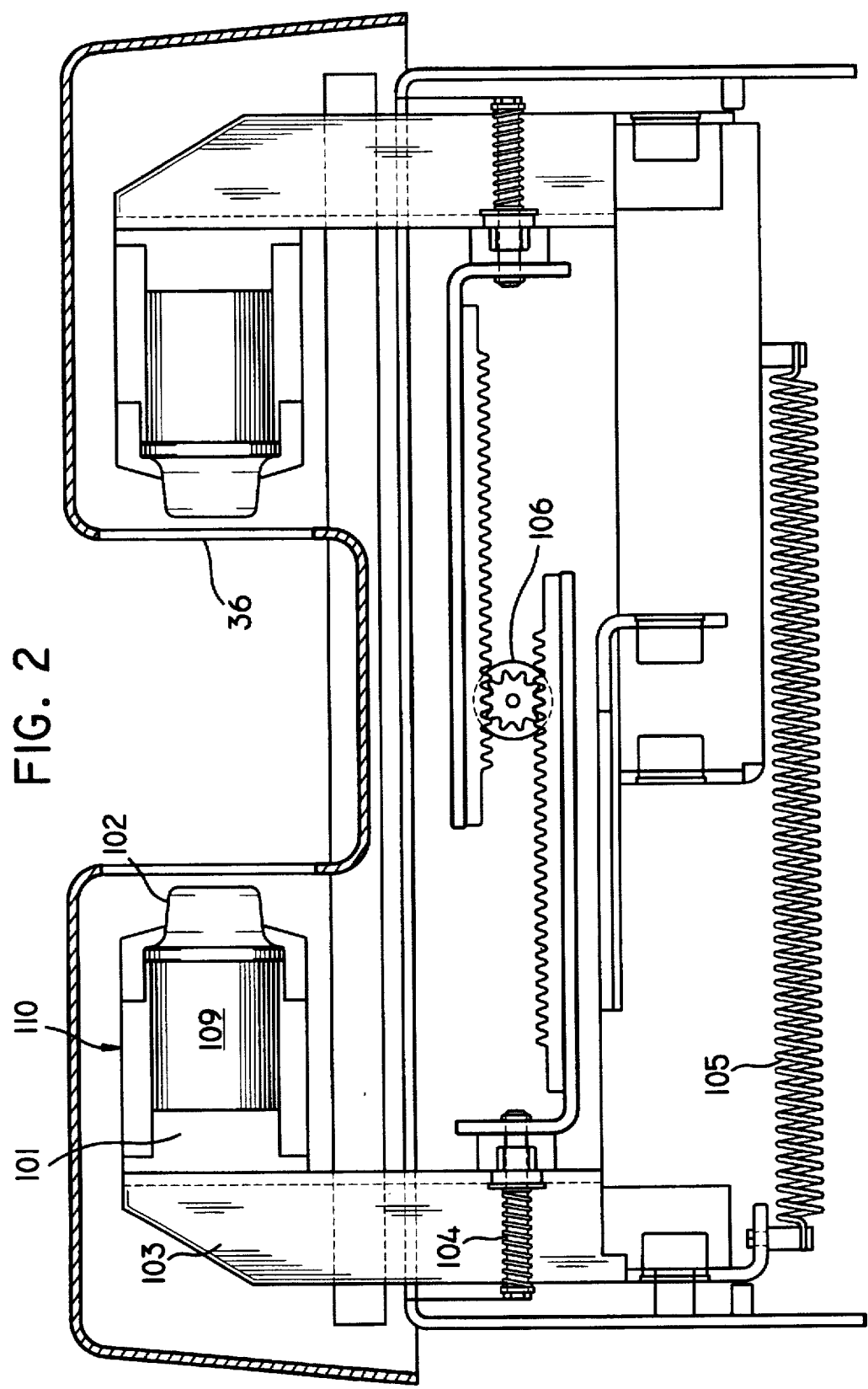

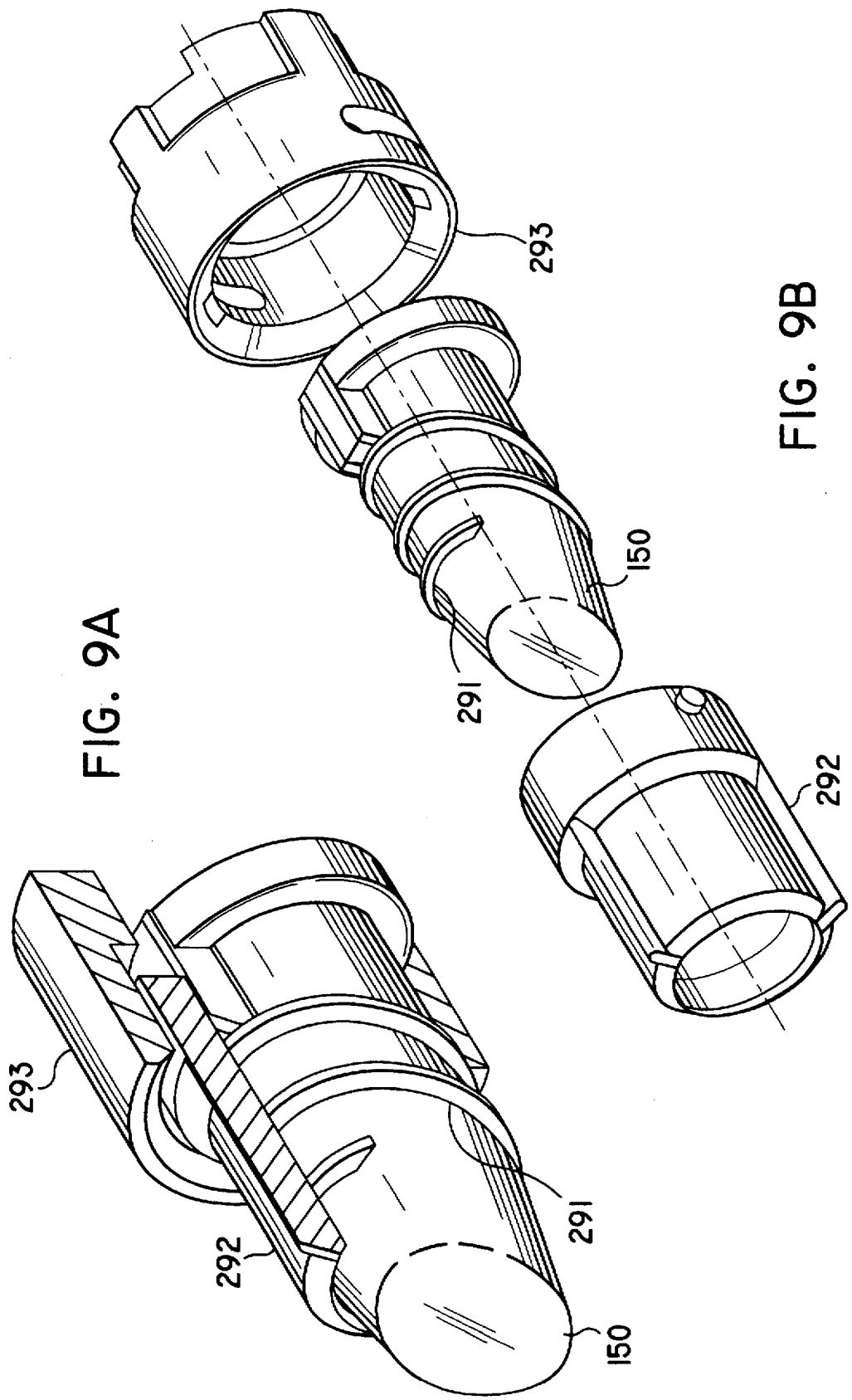

EQUIPMENT AND METHOD FOR CALIBRATION AND QUALITY ASSURANCE OF AN ULTRASONIC BONE ANAYLSIS APPARATUS

REFERENCE TO RELATED APPLICATIONS

The present invention is a continuation-in-part of application Ser. No. 08/477,580 filed on Jun. 7, 1995, now abandoned, which is hereby incorporated by reference herein as though fully set forth herein.

FIELD OF THE INVENTION

This invention relates to the field of ultrasonic analysis of bone tissue in humans, and more particularly to an improvement in the calibration and quality assurance of an ultrasonic bone analysis apparatus by using, for example, phantoms.

BACKGROUND OF THE INVENTION

The use of ultrasound in methods for detecting changes in bone characteristics is known. In particular, an ultrasound bone analysis apparatus has been used to analyze the properties of the heel bone or *os calcis*. The use of ultrasound is advantageous because it is non-invasive and is well-suited to repeated measurements or studies during medication since no ionizing radiation is used.

Precision and reliability of the ultrasonic bone analysis apparatus, as with other medical diagnostic instrumentation, are a matter of substantial importance. Therefore, the apparatus undergoes calibration and quality assurance regularly during its lifetime. Rather than using a human subject, the calibration and quality assurance is performed using a substitute medium that has specific ultrasonic properties. The calibration and quality assurance facilitate adjustment of the apparatus according to the specification of the instrument.

An ultrasonic bone analysis apparatus typically measures the rate of change of attenuation of ultrasound with frequency in the range of 200 to 600 kHz ("broadband ultrasound attenuation" or "BUA"), and also the speed of passage of acoustic waves ("speed of sound" or "SOS") through the bone. The BUA is a relative quantity calculated using a baseline signal as a reference of the transmitted signal entering the bone.

The baseline is typically acquired by measuring the signal after passage through a reference medium. Because the reference signal is used to assess the transmitted signal, the reference medium should minimally affect the ultrasonic signal.

Some existing ultrasonic bone analysis systems require immersing the foot of the patient in water. Several of these same "wet systems" use water as the reference medium. While water itself generally has a minimal distortive effect on the ultrasonic signal, its use necessitates preparation and cleanup, and is inconvenient for at least these reasons.

While some commercially available phantoms are suitable for monitoring temporal changes in scanner performance, the acoustic properties of these phantoms are typically significantly different from those of bones such as the *os calcis*. Therefore, these phantoms might not adequately mimic the human foot.

Heretofore, Clarke et al. proposed in "A Phantom for Quantitative Ultrasound of Trabecular Bone", 39 Phys. Med. Biol. 1677-87, to use a phantom as a substitute medium in a wet system.

The proposed phantom consists of a rectangular block manufactured from a mixture of liquid epoxy and gelatine particles. While the proposed phantom does have acoustic properties similar to bone and may be adequate for experimental purposes, Clarke et al. admit that the proposed phantom has a number of unsolved practical problems such as durability.

A phantom manufactured from an epoxy and glass bead mixture has also been used with a wet system. However, the manufacture of this phantom is believed to be complex and to require substantial supervision and control.

The measurement of SOS depends on the ambient conditions. Measuring accurately and comparing SOS data can be difficult due to the wide range of possible conditions, and such difficulties can be aggravated by imprecise control and determination of the conditions of the measurement.

Various media have been used for testing SOS measurements. Pure water and saline solution of various sodium chloride concentrations have been employed. However, the SOS for each of these substances varies according to temperature, each substance having a positive temperature coefficient. Therefore, using one of these substances in the testing of the SOS measurements has the disadvantage that temperature is an additional variable.

While ethyl alcohol is known to have a negative temperature coefficient of sound propagation, mixing ethyl alcohol with water tends to cancel the positive temperature coefficient of sound propagation in the water. A mixture of 17% ethyl alcohol by weight has a substantially zero temperature coefficient of sound propagation over a large range of temperatures.

OBJECTS AND SUMMARY OF THE INVENTION

Accordingly, it is an object of this invention to provide an improvement in the calibration and quality assurance of an ultrasonic bone analysis apparatus.

Another object of this invention is to provide a method of acquiring a reference signal which can be used for, amongst other purposes, calibration and quality assurance.

A further object of this invention is to provide a phantom for an ultrasound bone analysis apparatus which minimally affects the ultrasound signal so that the ultrasound signal transmitted through the phantom can be compared in both the time and frequency domain to a signal obtained when a foot is interposed between the coupling pads of the apparatus.

A further object of this invention is to provide a phantom that is convenient and easy to use.

A further object of this invention is to provide a phantom for an ultrasonic bone analysis apparatus which includes a white cylindrical plug cast inside a hard plastic housing. The plug is made of a soft elastic material having an attenuation-versus-frequency profile that is substantially flat. Furthermore, indentations having a shape complementary to respective transducer pads are provided on respective opposite sides of the plug.

A further object of this invention is to provide a phantom for an ultrasound bone analysis apparatus which approximates the ultrasonic properties of the human foot.

A further object of this invention is to provide a phantom that is uncomplicated and easily manufactured.

A further object of this invention is to provide a phantom for an ultrasonic bone analysis apparatus which is a block of polyurethane having an attenuation in the frequency range of 200–1000 kHz which is approximately the same as the human foot. Indentations having a shape complementary to the respective transducer pads are provided on respective opposite sides of the block.

A further object of this invention is to provide an phantom for an ultrasound bone analysis apparatus which has a predetermined SOS that is temperature-independent over the range of normal ambient temperatures.

A further object of this invention is to provide an phantom that is convenient and easily manufactured.

A further object of this invention is to provide an phantom for an ultrasonic bone analysis apparatus which includes a polyurethane housing having inner walls and indentations located on respective opposite sides of the housing. A mixture of ethyl alcohol and water which is 17% ethyl alcohol by weight fills an air-tight receptacle formed by the inner walls of the housing which prevents a change in alcohol concentration by evaporation of the alcohol or absorption of water by the mixture. The inner walls that are adjacent to the respective indentations are relatively thin compared to the distance between the inner walls.

A further object of this invention is to provide a method of calibration which accounts for variations in ultrasonic and electronic properties with temperature and time.

A further object of this invention is to provide a method of calibration which measures an ultrasonic signal transmitted through coupling pads mutually in contact, the measurement being relatively close in time to a measurement of a signal passing through a heel or a phantom interposed between the pads. The received signal passing through the mutually touching pads may be used as a reference for a BUA measurement. A measurement of a propagation time of the ultrasonic signal through the mutually touching pads may be used as a reference time for comparison to the signal passing through the heel, and thereby used for calculating a time of propagation through the heel. Because proximity in time is accompanied, presumptively, by proximity in ambient temperatures for the respective measurements, no correction for time or temperature drift between the measurements is required.

The received signal passing through the mutually touching pads may be compared to an ultrasonic signal measured at a known temperature, and the times of arrival of the two may be used to calculate an effective temperature of the pads. The effective temperature may be used to adjust temperature dependent coefficients of the BUA for the temporally-proximate measurements of the signals that pass through the heel or phantom.

A further object of this invention is to provide a method of calibration which measures a reflected signal produced by transmission of an ultrasonic signal through mutually contacting coupling pads, from a reflection by either the interface between the pads, a reflecting object placed in the pads, or a non-transmitting transducer face. A reflected signal is also produced by transmission of an ultrasonic signal through non-contacting coupling pads, from a reflection by either the interface between the pad and air, a reflecting object placed in the pads, or an object interposed between the pads. The reflected signal, in either instance, may be used to determine a time of propagation through all or part of the transmitting media, and scaled for comparison to the temporally-proximate measurement of the signal passing through the heel or phantom.

A further object of this invention is to monitor and control the environment of the ultrasound measurement.

According to the present invention, a transducer assembly of the apparatus is provided with a heater and the environment of the transmission media is controlled to maintain approximately a predetermined ambient temperature. For example, the predetermined temperature may be approximately body temperature. A temperature sensor is buried inside the coupling pad and thereby the temperature of the pad can be monitored.

A heater is provided in the phantoms according to the present invention, and thereby controlling the temperature at which an ultrasound measurement of the signal passing through the phantom is made. The phantoms may be controlled to maintain a predetermined temperature, such as approximately body temperature. A temperature sensor is buried inside the phantoms used for calibration or quality assurance according to the present invention, and thereby the temperature of the phantoms can be monitored.

BRIEF DESCRIPTION OF THE DRAWINGS

FIG. 2 is a sectional view of a transducer drive mechanism of the ultrasonic bone analysis apparatus.

FIG. 9A and FIG. 9B are a perspective view and an exploded view, respectively, of a transducer assembly of the ultrasonic bone analysis apparatus.

DETAILED DESCRIPTION

Ultrasonic Bone Analysis Apparatus

Figure 1:
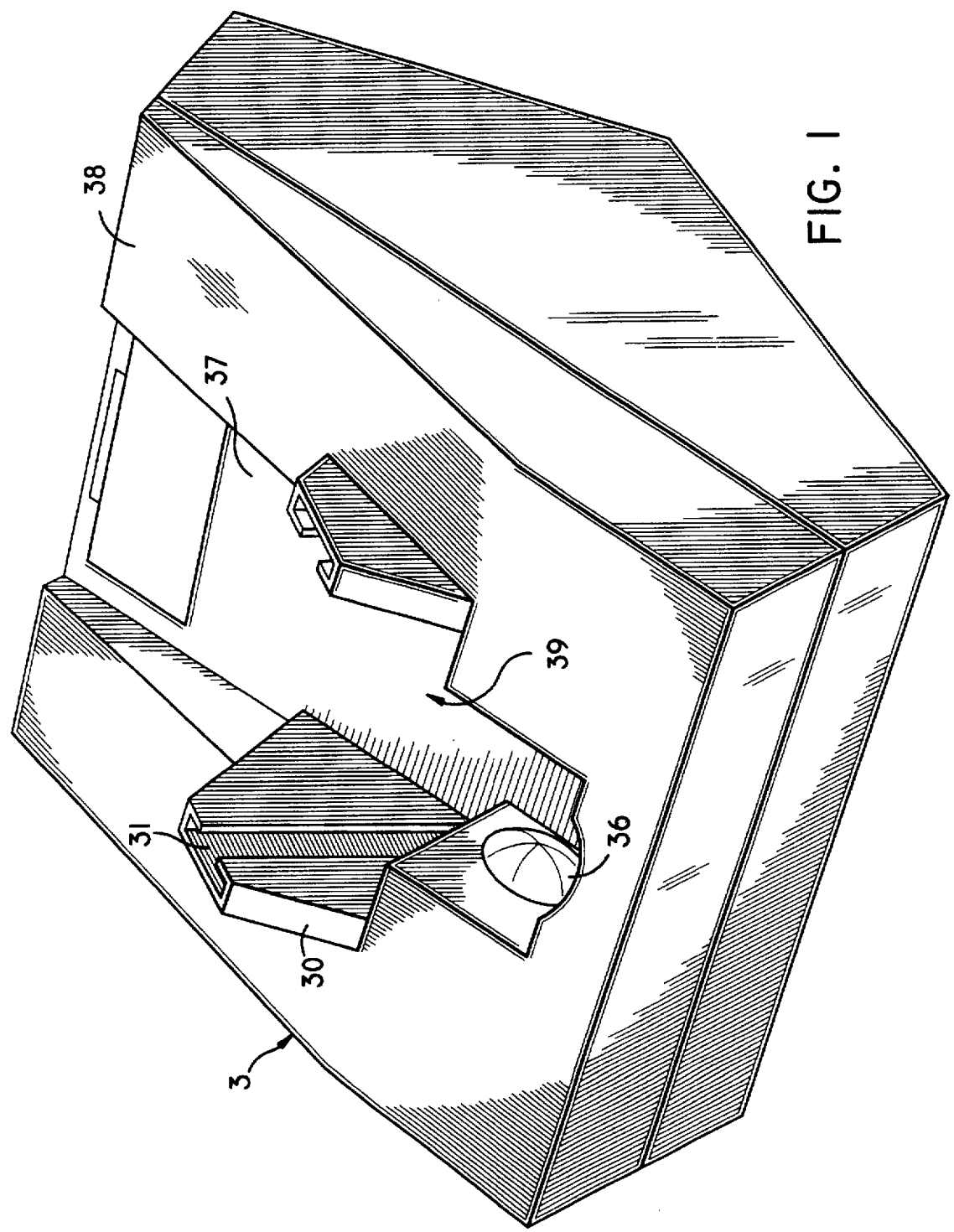
FIG. 1 is a perspective view of a foot well assembly of an ultrasonic bone analysis apparatus that can use phantoms according to the present invention.

Referring to FIG. 1, an ultrasonic bone analysis apparatus with which the phantoms according to the present invention can be used has a foot well assembly 3.

The foot well assembly 3 comprises a box cover 38 having a foot support 39, and foot well bottom 37. The foot support 39 has an area slightly larger than a human foot. Transducer ports 36 are located on the sides of the foot support 39, towards the rear. Bridge brackets 30 with respective channels 31 which are located along the sides of the foot support 39 facilitate the mounting of a shin guide assembly (not shown) for restraining the foot and lower leg.

Referring now to FIG. 2, a transducer drive mechanism of the ultrasonic bone analysis apparatus includes a pair of transducer assemblies 110. The transducer assemblies 110 include respective transducers 101, respective acoustical delay lines 109 and respective coupling pads 102.

The transducer assemblies 110 are mounted to respective carriages 103 that slide along a lateral-medial axis. The carriages 103 are provided with sufficient freedom of movement such that the respective coupling pads 102 can be brought into mutual contact. Respective compression springs 104 attached to the carriages 103 apply opposing lateral forces towards the center of the foot or phantom. The carriage/spring assembly is free floating and will center itself on the foot or phantom with equal pressure on both sides.

An extension spring 105 applies the initial pressure when the coupling pads 102 reach the phantom or the patient's foot. To adjust the pressure in small increments, a stepper motor with rack and pinion mechanism 106 will move a finite number of steps and compress the compression springs 104 that are attached to the respective carriages 103. The compression springs 104 will pull the respective transducers 101 and pads 102 inward at a force proportional to the spring rate and distance translated.

Figure 3B:
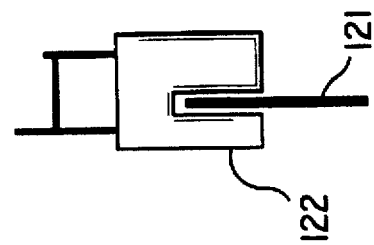
FIG. 3A and FIG. 3B are front and side views of a position encoder of the ultrasonic bone analysis apparatus.
Figure 3A:
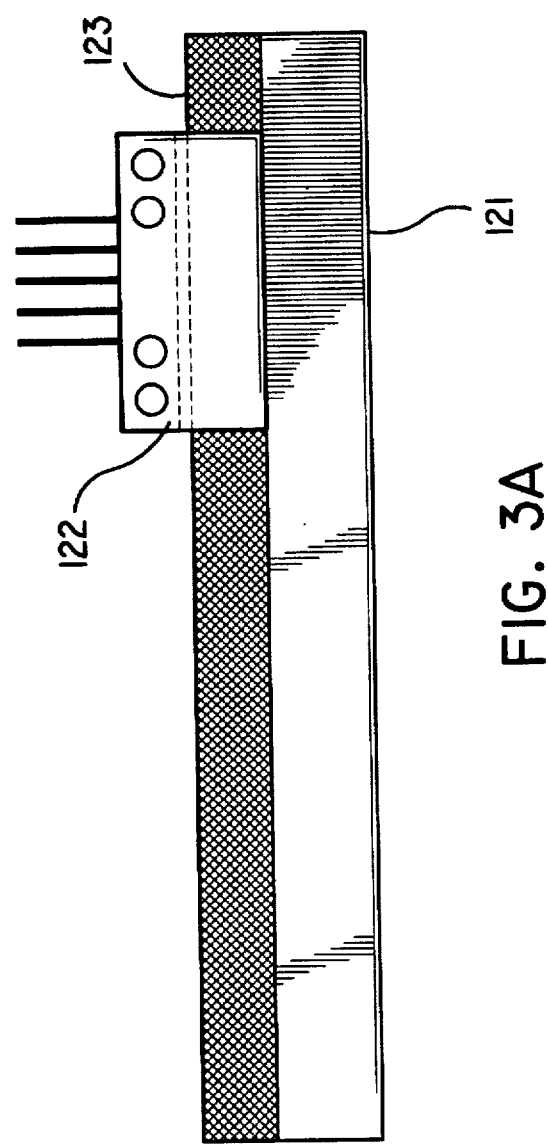

The distance between the transducers 101 is continuously measured by means of a position encoder 120 that is mechanically linked to the motion of the transducers 101. FIG. 3A and FIG. 3B illustrate respective front and side views of the position encoder 120. The position encoder has a code strip 121 mounted onto one of the carriages 103 and an optical encoder reader 122 mounted on the other of the carriages 103. As the distance between the transducers 101 changes, the code strip 121 moves between the slot of the optical encoder reader 122, and the optical reader 122 reads lines 123 of the code strip 121 as the lines 123 are traversed.

Figure 4:
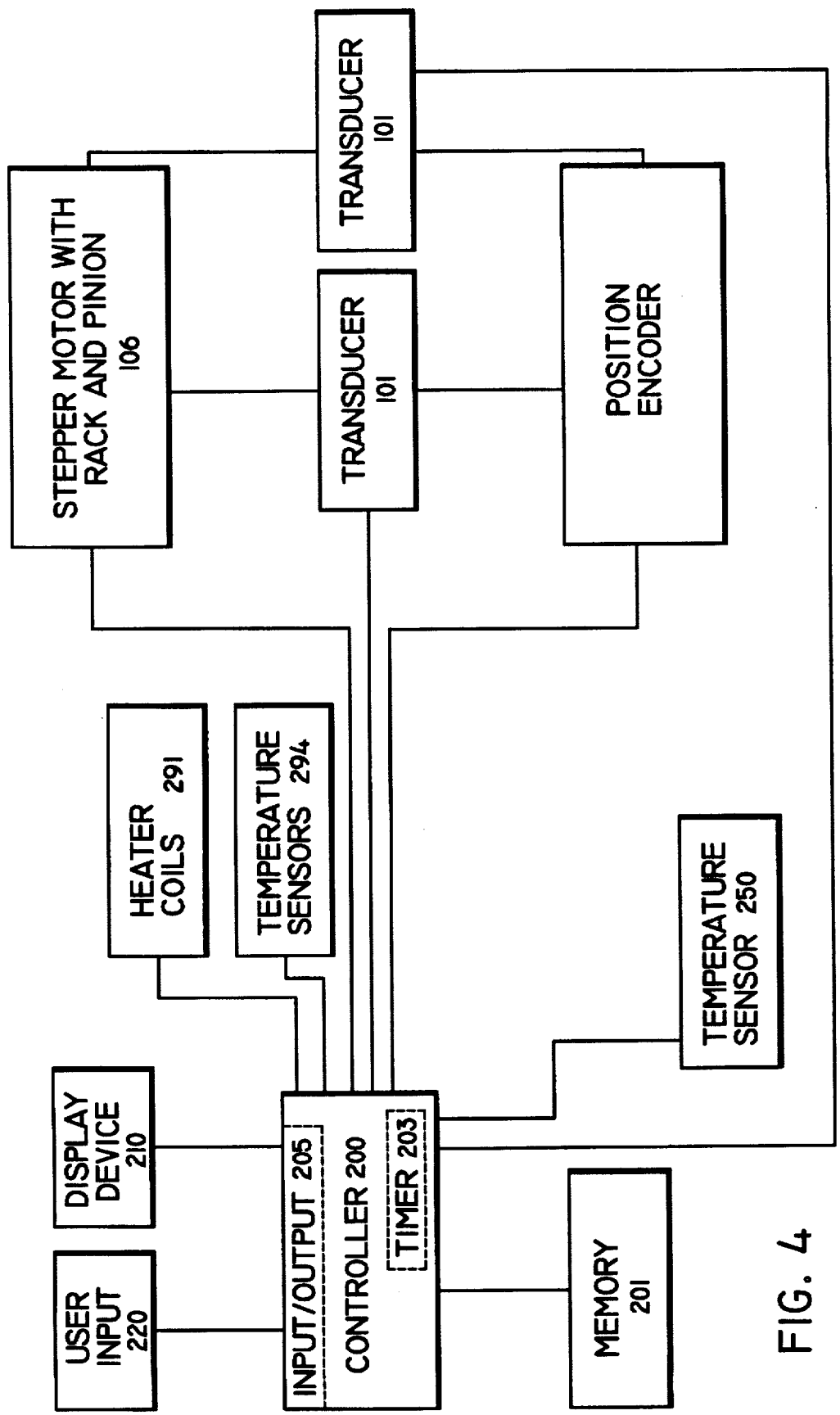
FIG. 4 is a block diagram showing control of the transducer drive mechanism of the ultrasonic bone analysis apparatus.

Referring to FIG. 4, the stepper motor with rack and pinion mechanism 106 under the control of controller 200 automatically positions transducers 101 against the patient's heel or the phantom with sufficient pressure to insure ultrasonic coupling. Signals received by the receiving transducer 101 are supplied to the controller 200. The microprocessor-based controller 200 controls the execution of system and application software and has a timer 203 and input/output circuitry 205 for interfacing with user input 220 and display device 210. Data and the system and application software are stored in memory 201 (e.g., RAM and ROM).

Preferably, the controller 200 controls the operations of the stepper motor 106 according to positional data supplied by the position encoder 120. The controller 200 monitors the position encoder 120 throughout the measurement to detect movement of the transducers 101 which may have a deleterious effect on the measurement.

Alternatively, the controller 200 determines the quality of the signals received by the receiving transducer 101 at least in part according to the attenuation of the signals, and controls the operations of the stepper motor 106 according to the quality of the signals received by the receiving transducer 101 and positional data supplied by the position encoder 120. These steps are repeated by the controller 200 until the signals received by the receiving transducer 101 achieve a predetermined quality.

The controller 200 determines other parameters of interest, including BUA and bone velocity. Also, the controller 200 uses timing data supplied by the timer 203 to determine the arrival time of the received ultrasonic signal combined with timing data for the reference signal which is stored in memory and the distance between the transducers as determined by the position encoder 120 to calculate the speed of the ultrasonic signals through the foot or phantom.

The controller 200 uses temperature readings from temperature sensor 250 to improve the accuracy of the position encoder measurements and correct for temperature dependent inaccuracy in the ultrasound measurement. For example, the controller 200 accounts for linear expansion of the encoder strip 121 by applying a temperature dependent term to the data supplied by the position encoder 120. Additionally, the controller 200 applies a temperature dependent term to correct an estimation of the time delay through the delay line 109 and the coupling pad 102. The controller 200 also applies a temperature dependent term to correct an estimation of the frequency-dependent attenuation of the coupling pad 102. Furthermore, the controller 200 uses the temperature reading to determine if the apparatus is operating within the specified environmental range allowed, and if not, the operator is informed that the apparatus is not ready to be used.

The coupling pads 102 have a durometer corresponding to a sufficiently flexible waveguide that can partially conform to the shape of a foot. The shape of the pads 102 conforms to the heel to eliminate any gaps between the foot and pad. The surfaces of the pads 102 which contact the transducers 101, the delay line 109, or the patent's skin is shaped at an angle to the propagation axis to reduce the acoustic reflection at the pad-to-skin interface by spreading the reflected energy over time and position.

Figure 5C:
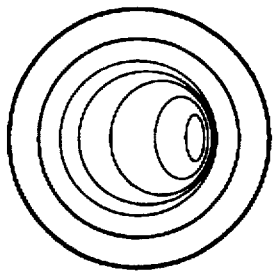
FIG. 5C is a contour diagram of an end of the pad/delay unit.
Figure 5A:
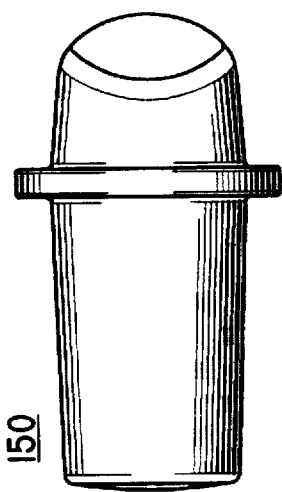
FIG. 5A and FIG. 5B are front and side views of a pad/delay unit of the ultrasonic bone analysis apparatus.
Figure 5B:
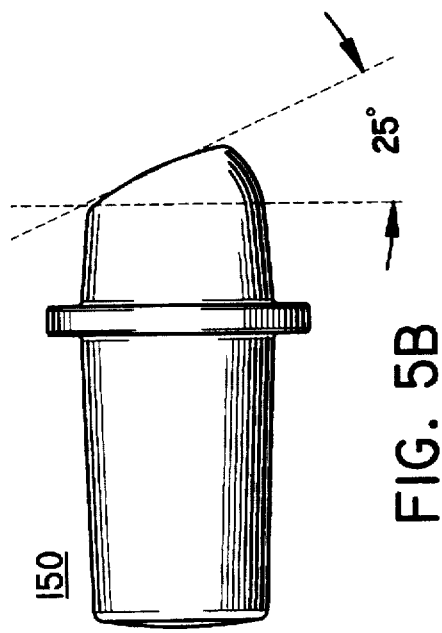

The coupling pad 102 and the delay line 109 are integrated into a single pad/delay unit 150 to reduce an extraneous reflection between a pad-to-delay-line interface. FIG. 5A and FIG. 5B illustrate top and side views of the pad/delay unit 150. The surface of the pad that contacts the patient's skin is shaped to expel air bubbles from the contact area when pressure is applied. FIG. 5C shows the contours of the surface of the pad/delay unit 150 which contacts the patient's skin.

A First Phantom

When executing software for calibration or quality assurance, the controller 200 via the display device 210 prompts the operator to insert a phantom in the foot support 39 of the foot well assembly 3.

Figure 6B:
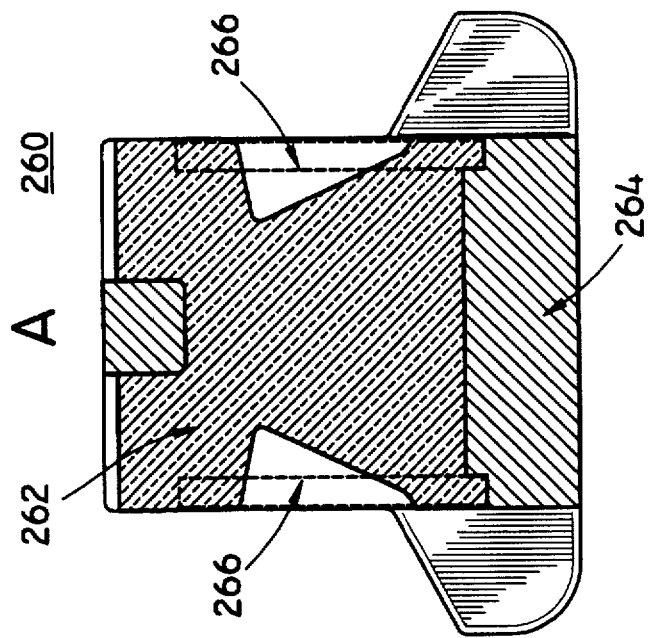
FIG. 6B is a sectional view of the first phantom taken essentially on the line A—A of FIG. 6A.
Figure 6A:
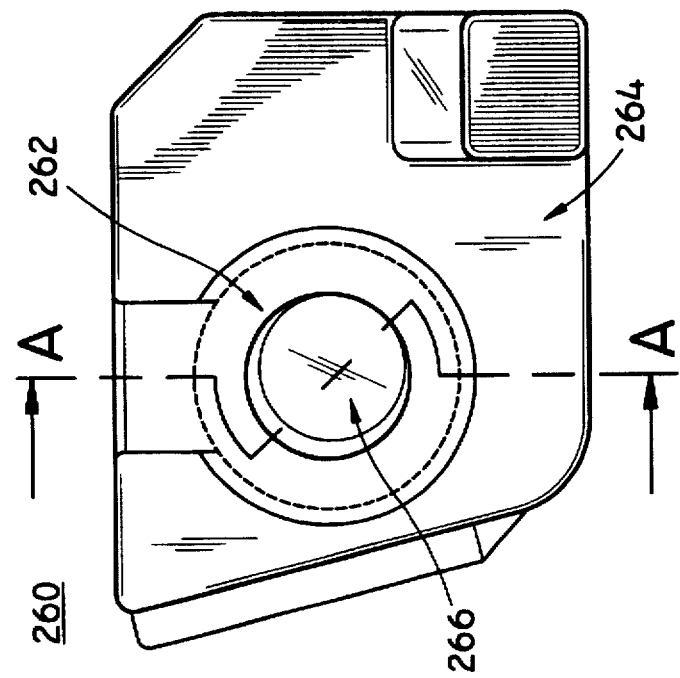
FIG. 6A is a front view of a first phantom according to the present invention.

FIGS. 6A and 6B illustrate a phantom 260 having a cylindrical plug 262 cast inside a hard plastic housing 264. The cylindrical plug 262 is a soft elastic material having a very low attenuation coefficient. The sound impedance of the soft elastic material is relatively close to that of soft human tissue. The attenuation-versus-frequency profile of the material in the frequency range of 200–1000 kHz is substantially flat. The soft elastic material has a minimal effect on the ultrasonic wave, and a predetermined SOS.

The soft material is preferably an elastomeric, white castable polyurethane set to a durometer of 10 to 50 Shore A. One such material is Ciba-Geigy TDT 178-34, which has a durometer of 15 Shore A and is also the preferred material of the transducer pads 150.

Indentations 266 are provided on opposite sides of the cylindrical plug 262 to accommodate the respective transducer pads 150. The shapes of the indentations 266 complement the shapes of the respective transducer pads 150. The hard plastic housing 264 positions the cylindrical plug 262 properly in relation to the transducer pads 150 of the apparatus. The complementary shapes of the pads 150 and respective indentations 266 of the cylindrical plug 262 facilitate the coupling of the pads 150 with the plug 262.

The phantom 260 has approximately the width of the typical female heel, and thereby mimics the conditions at

7 which the heel is measured. As a result, the reference signal spreads out in a pattern similar to that in an ultrasonic measurement of the heel.

When the phantom 260 is inserted in the apparatus, a signal is transmitted through the phantom. The controller 200 controls movement of the transducer assemblies 110 using feedback from the encoder 120. The received signal which had passed through the phantom 260 is used to calibrate the apparatus. Using timing data supplied by the timer 203, the controller 200 calculates the propagation time of the transmitted signal through the phantom 260. The controller 200 saves data of the received signal in the memory 201 and uses the saved data in subsequent calculations of BUA and SOS. The propagation time through the phantom 260 is used to calibrate a zero point of the apparatus, so that the propagation time through the foot can be calculated at a later time. The zero point is the difference between a predetermined time of propagation through the phantom 260, including an adjustment for temperature, and the measured time of propagation of a transmitted ultrasound signal through the phantom 260.

The controller 200 also determines the frequency spectrum of the received signal which is used in the BUA calculation. The received signal that passed through the phantom 260 is used as a baseline with which a signal that passes through the foot is compared. The BUA calculation will be explained in more detail hereinbelow.

The phantom 260 is also used for quality assurance of the apparatus. In this mode, the controller 200 calculates the drift of the apparatus by using the measurement of the current received signal that passed through the phantom 260 and recorded measurements of past received signals that had passed through the phantom 260 which are stored in memory 201. The drift is temperature-dependent. Therefore, because the human foot is typically at 98.6 degrees F. and the phantom 260 is at room temperature (generally between 60–90 degrees F.), the measured value is temperature-corrected according to the temperature reading from the temperature sensor 250.

A Second Phantom

Figure 7A:
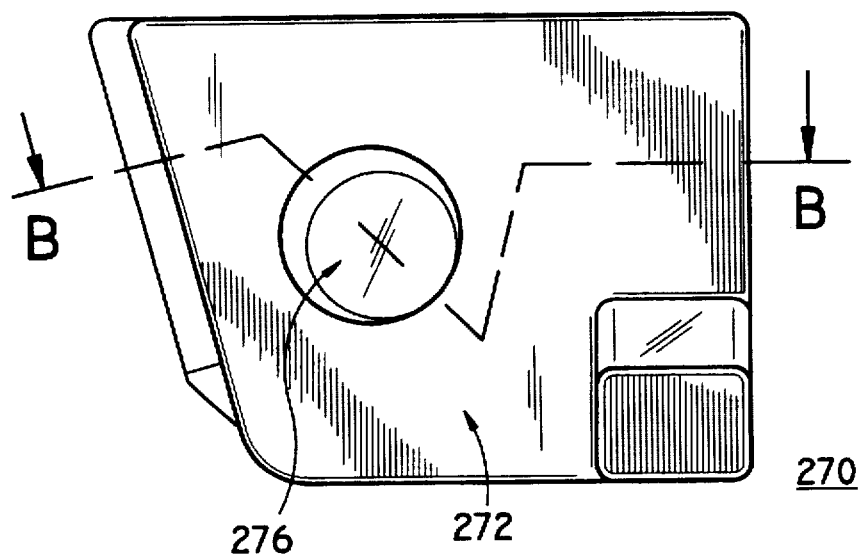
FIG. 7A is a front view of a second phantom according to the present invention.
Figure 7B:
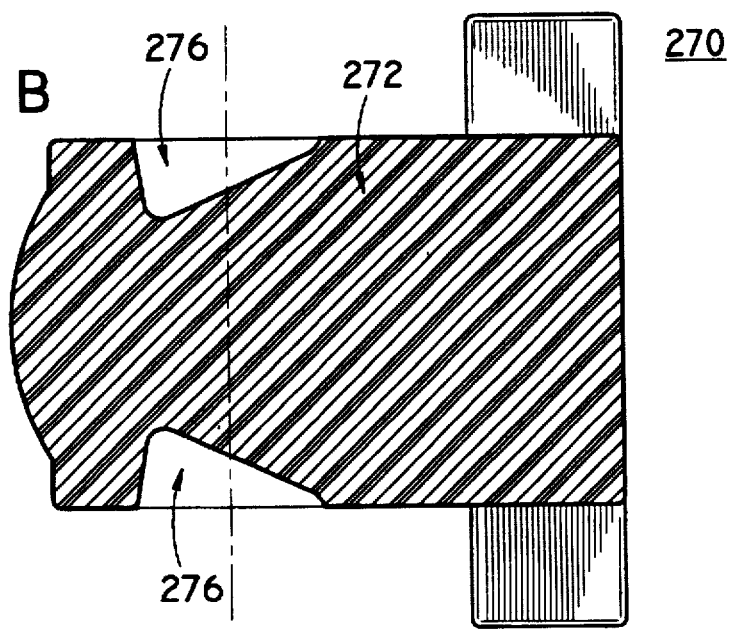
FIG. 7B is a sectional view of the second phantom taken essentially on the line B—B of FIG. 7A.

Referring to FIGS. 7A and 7B, a phantom 270 is provided to mimic the BUA of the human foot. The phantom 270 attenuates an ultrasonic wave in the frequency range of 200–1000 kHz by approximately the same amount as a human foot. The attenuation-versus-frequency profile of the phantom 270 is substantially linear in the frequency range of 200–600 kHz and is approximately 1 dB/MHz per mm. This profile is very similar to the attenuation-versus-frequency profile of the human foot.

The phantom 270 is a cut, castable, or otherwise manufactured block of material 272 having indentations 276 on opposite sides thereof to accommodate the respective transducer pads 150. The shapes of the indentations 276 complement the shapes of the respective transducer pads 150. The complementary shapes of the pads 150 and respective indentations 276 facilitate the coupling of the pads 150 with the block 272.

The phantom 270 also has approximately the width of the typical female heel, and thereby mimics the conditions at which the heel is measured. The block 272 is shaped to position the phantom 270 properly in relation to the transducer pads 150 when the phantom 270 is placed in the foot support 39 of the apparatus.

The block 272 is preferably a castable polyurethane. One such polyurethane is black and has approximately an 80 Shore A durometer. The polyurethane block is simple to manufacture and suitably mimics the human foot.

Software for calibration and quality assurance also measures a received signal that passed through the phantom 270. The steps for acquiring this measurement are similar to the steps for acquiring a measurement of the signal that passed through the phantom 260, as set forth hereinabove.

The received signals that passed through the phantom 270 are used for quality assurance of the apparatus for a BUA measurement. The BUA of a measured signal is calculated in the frequency domain. The measured signal and the reference signal in the time domain are transferred to respective frequency-domain counterparts |B(f)| and |R(f)| by performing a Fourier Transform or a Fourier Series calculation. The BUA is the slope of a line fit to a function A(f) in a specific frequency range. A(f) is defined as follows:

$$A(f) = 20 * \log_{10}(|B(f)|/|R(f)|).$$

A commonly used frequency range is 0.2 to 0.6 MHz.

As mentioned hereinabove, the reference signal may be obtained by measuring a signal that passed through the phantom 260. Magnitudes of respective frequency components of this reference signal are used as the reference |R(f)|.

The same reference signal may be used as the reference for calculating the BUA of a signal that passed through the phantom 270. In such a calculation, the magnitudes of the respective frequency components of the signal that passed through the phantom 270 are the |B(f)| of the measured signal.

The measurement of the received signal that passed through the phantom 270 is used by the quality assurance software to determine instrument drift. Because the phantom 270 mimics the human foot, the determined drift would reflect the expected drift when a human foot is analyzed using the apparatus. Again, because drift is temperature-dependent, the calculation includes a temperature correction term.

A Third Phantom

Figure 8A:
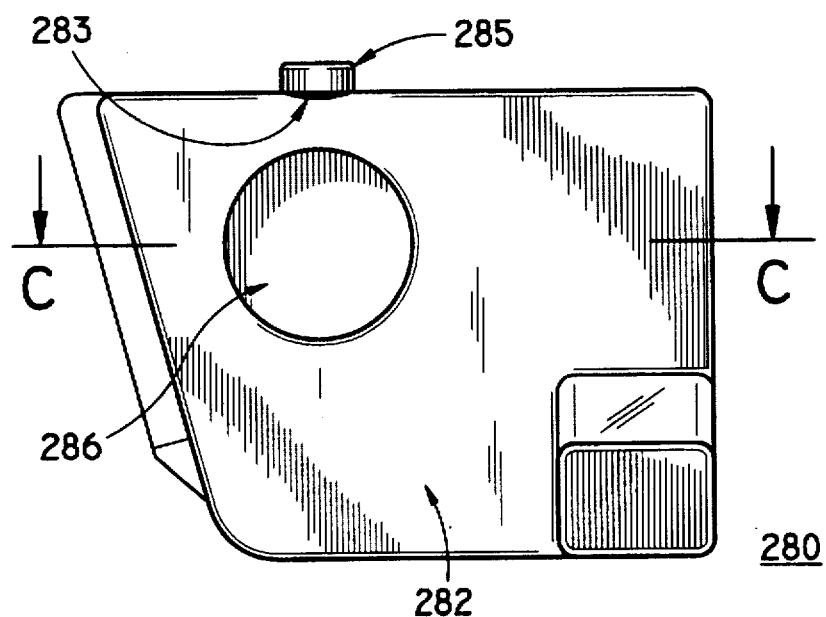
FIG. 8A is a front view of a third phantom according to the present invention.
Figure 8B:
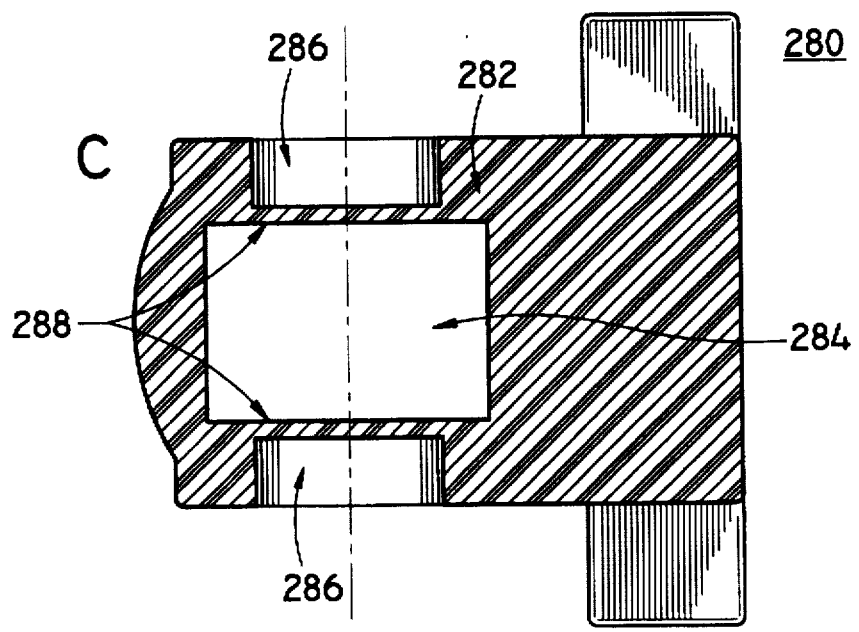
FIG. 8B is a sectional view of the third phantom taken essentially on the line C—C of FIG. 9A.

FIGS. 8A and 8B illustrate a phantom 280 that has a substantially zero temperature coefficient over a range of normal ambient temperatures.

The temperature-independent phantom 280 has a housing 282 containing a mixture of ethyl alcohol and water which is 17% ethyl alcohol by weight. The housing 282 has a filler port 283 through which the mixture is introduced. A cap 285 plugs the filler port 283 after the mixture fills a receptacle 284 formed by inner walls of the housing 282. The plugged receptacle 284 is air-tight to prevent a change in alcohol concentration by evaporation of the alcohol or absorption of water by the mixture. The housing 282 is made from preferably a polymer such as polyurethane which has a predetermined SOS.

Indentations 286 are provided on opposite sides of the housing 282 to accommodate the respective transducer pads 150. The bottoms of the respective indentations 286 are parallel to respective adjacent inner walls 288 of the housing. Therefore, the shapes of the indentations 286 do not complement the shape of the respective transducer pads 150. Nevertheless, because the pads 150 are elastomers, when the phantom is placed in the foot support 39, the transducer assemblies 110 can be moved under the control of controller 200 to compress the respective transducer pads 150 against the bottoms of the respective indentations 286 until there is adequate coupling. The compression of the transducer pads 150 does not affect the SOS measurement.

The housing 282 between each of the indentations 286 and the mixture should be relatively thin compared to the distance between the inner walls 288. The other portions of the housing 282 can be relatively thicker than the distance between the indentations 286 and the respective adjacent inner walls 288.

The phantom 280 also has approximately the width of the typical female heel, and thereby mimics the conditions at which the heel is measured. The housing 282 is shaped to position the phantom 280 properly in relation to the transducer pads 150 when the phantom 280 is placed in the foot support 39 of the apparatus.

Because the housing 282 encloses the fluid mixture, the phantom 280 is convenient to use. Furthermore, the phantom 280 having a polymer housing is easily manufactured.

The phantom 280 is used to calibrate the apparatus for the SOS calculation. Furthermore, the phantom 280 can be used for quality assurance to measure instrument drift. Because the phantom 280 has a predetermined SOS that is temperature-independent, the drift can be determined by comparing the measured value with the predetermined value. The steps for acquiring a signal that passed through the phantom 280 are similar to the steps for acquiring a signal that passed through the phantom 260, as set forth hereinabove.

The phantom 280 as described is substantially temperature-independent over a range of normal ambient temperatures because a mixture of ethyl alcohol and water which is 17% ethyl alcohol by weight is used. The temperature independence is preferred. Alternatively, the 17% mixture can be replaced by pure water or a mixture of water and ethyl alcohol which has a predetermined temperature coefficient. Measurements of an ultrasonic signal that passed through a phantom using pure water or the alternative mixture would need to be adjusted with an appropriate temperature-correction term which can be determined by one skilled in the art.

Mutually Contacting Transducer Pads

A reference signal can be obtained by another method using the ultrasonic bone analysis apparatus without a phantom. The controller 200 controls movement of the transducer assemblies 110 until the transducer pads 150 are mutually in contact. A received signal that passed through the mutually touching transducer pads can be used for many of the same purposes, which are described hereinabove, for which the received signals that passed through the phantom 260 is used.

It is desirable to obtain calibration measurements that account for variations in ultrasonic and electronic properties according to respective variation in temperature and time. The measurement of the received signal that passed through the mutually contacting coupling pads is obtained relatively close in time to a measurement of a signal passing through a heel or a phantom interposed between the pads. Because proximity in time is accompanied, presumptively, by proximity in ambient temperatures for the respective measurements, no correction for time or temperature drift between the measurements is required. Therefore, the measured signal obtained while the pads 150 are mutually touching may be used to compare with the signal that passed through the heel to measure quantities that are of interest to bone quality without contamination of the measurement by the ambient temperature at which the measurement was taken.

The received signal that passed through the mutually touching pads may be used as a reference for a BUA measurement. Additionally, a propagation time of the ultrasonic signal through the mutually touching pads is measured and may be used as a reference time for propagation through the pads. The reference time measurement may be compared to the measurement of the signal that passed through the heel to determine a time of propagation through the heel. The calculated time of propagation through the heel along with information about the width of the heel are used to calculate a SOS of the heel.

The received signal that passed through the mutually touching pads may be compared to an ultrasonic signal measured at a known temperature, and the time of arrival of the two may be used to calculate an effective temperature of the pads. The effective temperature may be used to adjust temperature-dependent coefficients of the BUA for the temporally-proximate measurements of the signals that pass through the heel or phantom.

The transmission of an ultrasonic signal through mutually contacting coupling pads may produce a reflected signal from a reflection by either the interface between the pads, a reflecting object placed in the pads, or a non-transmitting transducer face. A measurement of the reflected signal may be used to determine a time of propagation through all or part of the transmitting media, including the transducer 101 and the transducer pads 150, and scaled for comparison to the temporally-proximate measurement of the signal passing through the heel or phantom.

Transmission of an ultrasonic signal through non-contacting coupling pads can also produce a reflected signal. A measurement of the reflected signal produced from a reflection by either the interface between the pad and air, a reflecting object placed in the pads, or an object interposed between the pads may be used for the same purposes as the measurement of the reflected signal produced by transmitting through mutually contacting coupling pads.

Other Provisions Related to Temperature

The present invention makes other provisions for controlling the environment of the transmission media.

Referring to FIGS. 9A and 9B, the transducer assembly 110 includes a heater coil 291, a cap 292, and a housing 293. The heater coil 291 is wrapped around a portion of the coupling pad 150. The cap 292 isolates the heater coil 291 from the housing 293. Furthermore, a temperature sensor 294 (shown in FIG. 4) is buried inside the coupling pad 150, and thereby the temperature of the pad 150 can be monitored. The controller 200 monitors a temperature reading supplied by the temperature sensor 294 and controls the heater coil 291 accordingly to maintain the pads 150 at a predetermined temperature, such as approximately body temperature.

Figure 10:
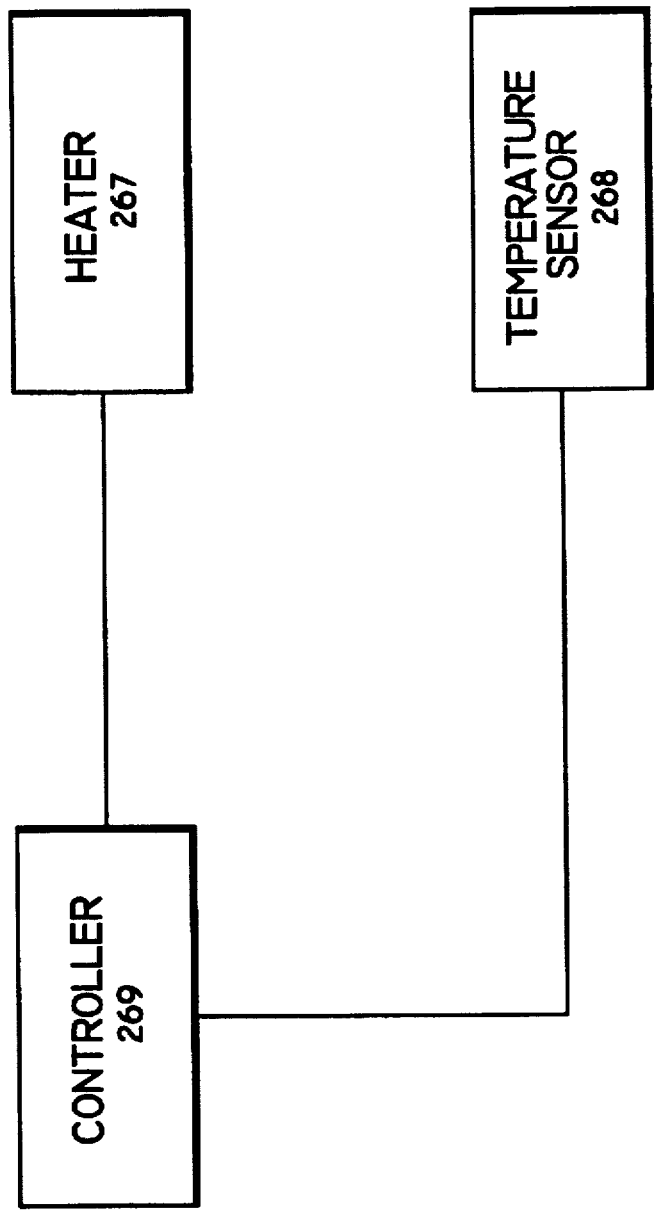
FIG. 10 is a block diagram showing control of temperature of a phantom of the present invention.

Referring to FIG. 10, the phantoms 260, 270 and 280 which are used for calibration or quality assurance according to the present invention are preferably also provided with respective heaters 267, temperature sensors 268 and controllers 269. The temperature sensor 268 are also buried inside the respective phantoms and supply readings of the respective temperatures of the respective phantoms. The controllers 269 monitor the respective temperature readings of the respective temperature sensors 268 and controls the respective heaters accordingly to maintain a predetermined value. For example, the temperature of the phantom can be maintained at approximately body temperature to simulate the measurement of the heel. The temperature at which an ultrasound measurement of the signal passing through one of the phantoms thereby can be controlled.

Coupling gel can be used with the phantoms of the present invention. The coupling gel applied between the phantom and coupling pads does not affect the efficacy of the phantoms. While the typical commercially available water-based coupling gel can be used, a non-aqueous jelly is preferred. For example, petroleum jelly can be used as a coupling gel.

The present invention has been described by using three separate phantoms. However, the relevant features of the respective phantoms can be combined into a single phantom. For example, the single phantom can have the configuration of one of the above-described phantoms, and includes combined materials to provide the above-described properties of the three phantoms so that a received signal that passed through the single phantom has signal characteristics corresponding to these properties.

Having described the preferred phantoms of the present invention with reference to the accompanying drawings, it is to be understood that the invention is not limited to that precise embodiment and that various changes and modifications thereof could be effected by one skilled in the art without departing from the spirit or scope of the novel concepts of the invention, as defined in the appended claims.

What is claimed is:

1. A phantom for an ultrasound bone analysis apparatus having a foot well and a plurality of transducer pads, comprising:

a plug cast having a plurality of indentations located on a respective plurality of opposite sides thereof, the plurality of indentations having a respective plurality of shapes complementary to a respective plurality of shapes of the respective plurality of transducer pads, the plug also having an attenuation-versus-frequency profile that is substantially flat in a frequency range of between about 200 kHz and about 1000 kHz and a sound impedance that approximates that of soft human tissue.

2. The phantom according to claim 1, wherein a speed of sound through the plug is predetermined.

3. The phantom according to claim 1, wherein the plug is made of an elastomeric material.

4. The phantom according to claim 1, wherein the plug is made of an elastomeric castable polyurethane having a durometer between 10 and 50 Shore A.

5. The phantom according to claim 1, further comprising a housing, the plug being cast inside the housing, wherein when the phantom is placed in the foot well of the ultrasonic bone analysis apparatus, the housing positions the plug properly in relation to the plurality of transducer pads.

6. The phantom according to claim 1, wherein the complementary shapes of the plurality of transducer pads and the respective plurality of indentations facilitate coupling of the plurality of transducer pads to the plug.

7. The phantom according to claim 1, wherein the phantom has a width of a typical female heel, and an ultrasound signal passing through the phantom spreads out in a pattern approximating that of an ultrasound signal passing through a human heel.

8. The phantom according to claim 1, wherein an ultrasound signal received through one of the plurality of transducer pads which passed through the phantom is used to calibrate the ultrasound bone analysis apparatus.

9. The phantom according to claim 1, wherein a propagation time of an ultrasound signal received through one of the plurality of transducer pads which passed through the phantom is used to calibrate a zero point of the ultrasound bone analysis apparatus.

10. The phantom according to claim 1, wherein an ultrasound signal received through one of the plurality of transducer pads which passed through the phantom is used as a baseline for calculating BUA.

11. The phantom according to claim 1, wherein an ultrasound signal received through one of the plurality of transducer pads which passed through the phantom is used for at least one of determining and correcting a drift of the ultrasound bone analysis apparatus.

12. The phantom according to claim 1, further comprising:

a heater for maintaining the phantom at a predetermined temperature; and a temperature sensor for measuring the temperature of the phantom.

13. A phantom for an ultrasound bone analysis apparatus having a foot well and a plurality of transducer pads, comprising:

a block of material having a plurality of indentations located on a respective plurality of opposite sides thereof, the plurality of indentations having a respective plurality of shapes complementary to the respective plurality of transducer pads, and the block having an attenuation in a frequency range of between about 200 kHz and about 1000 kHz which approximates that of a human foot.

14. The phantom according to claim 13, wherein the block is made of a castable polyurethane.

15. The phantom according to claim 13, wherein the phantom has an attenuation-versus-frequency profile that is substantially linear in a frequency range of 200–600 kHz and is approximately 1 dB/MHz per mm.

16. The phantom according to claim 13, wherein the complementary shapes of the respective plurality of transducer pads and the respective plurality of indentations facilitate coupling of the plurality of transducer pads to the phantom.

17. The phantom according to claim 13, wherein the phantom has a width of a typical female heel.

18. The phantom according to claim 13, wherein the block is shaped such that when the phantom is placed in the foot well of the ultrasonic bone analysis apparatus, the phantom is positioned properly in relation to the plurality of transducer pads of the ultrasonic bone analysis apparatus.

19. The phantom according to claim 13, wherein an ultrasound signal received through one of the plurality of transducer pads which passed through the phantom is used to calibrate the apparatus for a BUA calculation.

20. The phantom according to claim 13, wherein an ultrasound signal received through one of the plurality of transducer pads which passed through the phantom is used for at least one of determining and correcting a drift of the ultrasound bone analysis apparatus.

21. The phantom according to claim 13, further comprising:

a heater for maintaining the phantom at substantially a predetermined temperature; and a temperature sensor for monitoring the temperature of the phantom.

22. A phantom for an ultrasound bone analysis apparatus having a foot well and a plurality of transducer pads, comprising:

a housing having a plurality of inner walls and a plurality of indentations located on a respective plurality of opposite sides of the housing, the plurality of indentations having a respective plurality of bottoms parallel to respective adjacent ones of the plurality of inner walls of the housing; and a mixture of ethyl alcohol and water which is contained by an air-tight receptacle formed from the plurality of inner walls of the housing, the mixture having a predetermined ratio of alcohol and water and a predetermined SOS that is substantially temperature-independent, and air-tight receptacle preventing a change in alcohol concentration by evaporation of the alcohol or absorption of water by the mixture.

23. The phantom according to claim 22, wherein the mixture is substantially 17% ethyl alcohol by weight.

24. The phantom according to claim 22, wherein the housing is made from a polymer which has a predetermined SOS.

25. The phantom according to claim 22, wherein the housing is made from a polyurethane which has a predetermined SOS.

26. The phantom according to claim 22, wherein the ones of the plurality of inner walls which are adjacent to the respective plurality of indentations are relatively thin compared to the distance between the ones of the plurality of inner walls which are adjacent to the respective plurality of indentations.

27. The phantom according to claim 22, wherein the phantom has a width of a typical female heel.

28. The phantom according to claim 22, wherein the housing is shaped to position the phantom properly in relation to the plurality of transducer pads.

29. The phantom according to claim 22, wherein an ultrasound signal received through one of the plurality of transducer pads which passed through the phantom is used to calibrate the apparatus for a SOS calculation.

30. The phantom according to claim 22, wherein an ultrasound signal received through one of the plurality of transducer pads which passed through the phantom is used for quality assurance including at least one of determining and correcting instrument drift by calculating a SOS based on the received signal and comparing the calculated SOS with the predetermined SOS.

31. The phantom according to claim 22, wherein the mixture is pure water.

32. A method of calibrating an ultrasound bone analysis apparatus having a foot well and a plurality of transducer assemblies with a respective plurality of transducer pads, comprising the steps of:

placing in the foot well a first phantom having an attenuation-versus-frequency profile that is substantially flat in a frequency range of between about 200 kHz and about 1000 kHz and a sound impedance that approximates that of soft human tissue;

adjusting the plurality of transducer assemblies;

transmitting through the first phantom via one of the plurality of transducer pads an ultrasound signal;

receiving via another one of the plurality of transducer pads a signal that passed through the first phantom; and using the received signal that passed through the first phantom as a baseline for calculating a BUA.

33. The method according to claim 32, further comprising the steps of:

measuring a propagation time of the received signal that passed through the first phantom; and using the propagation time to calibrate a zero point of the apparatus.

34. The method according to claim 33, further comprising the steps of:

measuring a temperature of the first phantom; and adjusting the zero point according to the measured temperature of the first phantom.

35. The method according to claim 32, further comprising the step of using the received signal that passed through the first phantom for at least one of determining and correcting a drift of the apparatus.

36. The method according to claim 32, further comprising the steps of:

removing the first phantom from the foot well;

placing in the foot well a second phantom having an attenuation in a frequency range of 200–1000 kHz which approximates that of a human foot, including an attenuation-versus-frequency profile that is substantially linear in a frequency range of 200–600 kHz and is approximately 1 dB/MHz per mm;

adjusting the plurality of transducer assemblies;

transmitting through the second phantom via the one of the plurality of transducer pads a second ultrasound signal;

receiving via the another one of the plurality of transducer pads a second signal that passed through the second phantom; and using the second received signal that passed through the second phantom to calibrate the apparatus for a BUA monitoring.

37. The method according to claim 36, wherein the received signal that passed through the first phantom is also used for quality assurance of the apparatus for a BUA measurement.

38. A method of calibrating an ultrasound bone analysis apparatus having a foot well and a plurality of transducer assemblies with a respective plurality of transducer pads, comprising the steps of:

placing in the foot well a phantom having an attenuation in a frequency range of between about 200 kHz and about 1000 kHz which approximates that of a human foot, including an attenuation-versus-frequency profile that is substantially linear in a frequency range of between about 200 kHz and about 600 kHz and is approximately 1 dB/MHz per mm;

adjusting the plurality of transducer assemblies;

transmitting through the phantom via one of the plurality of transducer pads an ultrasound signal;

receiving via another one of the plurality of transducer pads a signal that passed through the phantom; and using the received signal that passed through the phantom to calibrate the apparatus for a BUA calculation.

39. The method according to claim 38, further comprising the step of using the received signal that passed through the phantom for at least one of determining and correcting a drift of the apparatus.

40. A method of calibrating an ultrasound bone analysis apparatus having a foot well and a plurality of transducer assemblies with a respective plurality of transducer pads, comprising the steps of:

placing in the foot well a phantom having a predetermined SOS that is substantially temperature-independent;

adjusting the plurality of transducer assemblies;

transmitting through the phantom via one of the plurality of transducer pads an ultrasound signal;

receiving via another one of the plurality of transducer pads a signal that passed through the phantom; and using the received signal that passed through the phantom for at least one of determining and correcting a drift of the apparatus.

41. The method according to claim 40, further comprising the step of using the received signal that passed through the phantom to calibrate the apparatus for a SOS calculation.

42. The method according to claim 40, wherein the drift of the apparatus is determined by calculating a SOS based on the received signal that passed through the phantom and comparing the calculated SOS with the predetermined SOS.

43. A method of calibrating an ultrasound bone analysis apparatus having a plurality of transducer assemblies with a respective plurality of transducers and a respective plurality of transducer pads, comprising the steps of:

adjusting the plurality of transducer assemblies until the plurality of transducer pads are mutually in contact;

transmitting an ultrasound signal through one of the plurality of transducers; and receiving a signal corresponding to the transmitted signal through another one of the plurality of transducers.

44. The method according to claim 43 further comprising the step of using the received signal as a baseline for calculating BUA.

45. The method according to claim 43 further comprising the steps of:

measuring a propagation time of the received signal; and using the propagation time as a reference time of propagation through the plurality of transducer pads.

46. The method according to claim 45 further comprising the step of comparing the reference time of propagation through the plurality of transducer pads with a temporally-proximate measurement of an ultrasonic signal that passed through a patient's heel to determine a time of propagation through the heel.

47. The method according to claim 43 further comprising the steps of:

comparing a time of arrival of the received signal with a predetermined time of arrival of an ultrasonic signal measured at a predetermined temperature to calculate an effective temperature of the plurality of pads; and using the calculated effective temperature to adjust temperature-dependent coefficients of a BUA of a temporally-proximate measurement of an ultrasonic signal that passed through a patient's heel.

48. The method according to claim 43 further comprising the steps of:

measuring a reflected signal from a reflection by at least one of an interface between the plurality of transducer pads, a reflecting object placed in the plurality of transducer pads, and a face of one of the plurality of transducers which was not transmitting; and using the measured reflected signal to determine a time of propagation through at least one of the plurality of transducers and the plurality of transducer pads.

49. An apparatus for performing ultrasonic bone analysis comprising:

a foot well assembly having a foot well for resting a patient's foot;

a transducer drive mechanism including a plurality of transducer assemblies having a plurality of respective transducers and a plurality of respective coupling pads, at least one of the plurality of transducers supplying ultrasonic signals and at least another one of the plurality of transducers receiving ultrasonic signals corresponding to the transmitted signals, and the plurality of transducer assemblies being adjustable to respective positions such that the plurality of respective coupling pads are in mutual contact; and a controller for controlling the positioning of the plurality of transducer assemblies to achieve ultrasonic coupling, controlling the ultrasonic signals transmitted by at least the one of the plurality of transducers, performing calibration including calibrating a zero point of the apparatus, and performing quality assurance including at least one of determining and correcting a drift of the apparatus.

50. The apparatus according to claim 49, further comprising a phantom having an attenuation-versus-frequency profile that is substantially flat in a frequency range of 200 to 1000 kHz and a sound impedance that approximates that of soft human tissue, wherein the controller uses a received signal as a baseline for calculating BUA, the received signal being an ultrasonic signal received by the another one of the plurality of transducers which was transmitted by the one of the plurality of transducers and passed through the phantom.

51. The apparatus according to claim 49, further comprising a phantom having an attenuation-versus-frequency profile that is substantially flat in a frequency range of 200 to 1000 kHz and a sound impedance that approximates that of soft human tissue, wherein the controller measures a propagation time of an ultrasonic signal received by the another one of the plurality of transducers which was transmitted by the one of the plurality of transducers and passed through the phantom, and uses the measured propagation time to calibrate the zero point of the apparatus.

52. The apparatus according to claim 49, further comprising a phantom having an attenuation-versus-frequency profile that is substantially flat in a frequency range of 200 to 1000 kHz and a sound impedance that approximates that of soft human tissue, wherein the controller uses a received signal for at least one of determining and correcting the drift of the apparatus, the received being an ultrasonic signal received by the another one of the plurality of transducers which was transmitted by the one of the plurality of transducers and passed through the phantom.

53. The apparatus according to claim 49, further comprising a phantom having an attenuation in a frequency range of 200–1000 kHz which approximates that of a human foot, wherein the controller uses a received signal to calibrate the apparatus for a BUA calculation, the received signal being an ultrasonic signal received by the another one of the plurality of transducers which was transmitted by the one of the plurality of transducers and passed through the phantom.

54. The apparatus according to claim 49, further comprising a phantom having an attenuation in a frequency range of 200–1000 kHz which approximates that of a human foot, wherein the controller uses a received signal for at least one of determining and correcting the drift of the apparatus, the received signal being an ultrasonic signal received by the another one of the plurality of transducers which was transmitted by the one of the plurality of transducers and passed through the phantom.

55. The apparatus according to claim 49, further comprising a phantom having a predetermined SOS that is substantially temperature-independent, wherein the controller uses a received signal for calibrating the apparatus for a SOS calculation, the received signal being an ultrasonic signal received by the another one of the plurality of transducers which was transmitted by the one of the plurality of transducers and passed through the phantom.

56. The apparatus according to claim 49, further comprising a phantom having a predetermined SOS that is substantially temperature-independent, wherein the controller uses a received signal for at least one of determining and correcting the drift of the apparatus, the received signal being an ultrasonic signal received by the another one of the plurality of transducers which was transmitted by the one of the plurality of transducers and passed through the phantom.

57. The apparatus according to claim 49, wherein the controller adjusts the positioning of the plurality of transducer assemblies until the plurality of transducer pads are mutually in contact, and uses a received signal as a baseline for calculating BUA, the received signal being an ultrasound signal received by the another one of the plurality of transducers which was transmitted by the one of the plurality of transducers and passed through the plurality of mutually contacting transducer pads.

58. The apparatus according to claim 49, wherein the controller adjusts the positioning of the plurality of transducer assemblies until the plurality of transducer pads are mutually in contact, determines a propagation time of an ultrasound signal received by the another one of the plurality of transducers which was transmitted by the one of the plurality of transducers and passed through the plurality of mutually contacting transducer pads, and uses the propagation time to calibrate the zero point of the apparatus.

59. The apparatus according to claim 49, wherein the controller adjusts the positioning of the plurality of transducer assemblies until the plurality of transducer pads are mutually in contact, and uses for at least one of determining and correcting the drift of the apparatus, the received signal being an ultrasound signal received by the another one of the plurality of transducers which was transmitted by the one of the plurality of transducers and passed through the plurality of mutually contacting transducer pads.

60. The apparatus according to claim 49, the plurality of transducer pads having:

a plurality of heaters for maintaining the plurality of respective transducer pads at substantially a predetermined temperature; and a plurality of temperature sensors for measuring the temperature of the plurality of respective transducer pads, wherein the controller monitors the measured temperature of the transducer pads which is supplied by the plurality of temperature sensors and controls the plurality of respective heaters accordingly to maintain the plurality of respective transducer pads at the predetermined temperature.

61. A phantom for an ultrasound bone analysis apparatus having a foot well and a plurality of transducer pads, comprising:

a block of material having a predetermined SOS that is substantially temperature-independent and a sound impedance that approximates that of soft human tissue, and the block having at least one of an attenuation-versus-frequency profile that is substantially flat in a frequency range of between about 200 kHz and about 1000 kHz and an attenuation in a frequency range of between about 200 kHz and about 1000 kHz which approximates that of a human foot.

* * * * *